United States Patent [19]

Takayama

[11] 4,324,466
[45] Apr. 13, 1982

[54] LIGHT SOURCE APPARATUS FOR ENDOSCOPE

[75] Inventor: Syuichi Takayama, Hachioji, Japan

[73] Assignee: Olympus Optical Co., Ltd., Tokyo, Japan

[21] Appl. No.: 175,504

[22] Filed: Aug. 5, 1980

[30] Foreign Application Priority Data

Sep. 3, 1979 [JP] Japan .............................. 54/112635

[51] Int. Cl.³ .................... G03B 7/16; G03B 29/00
[52] U.S. Cl. ......................................... 354/33; 354/62
[58] Field of Search ............... 354/32, 33, 62, 63, 354/75, 76, 126; 128/6, 8

[56] References Cited

U.S. PATENT DOCUMENTS 4,086,583 4/1978 Takahashi .......................... 354/62
4,153,356 5/1979 Hama ................................ 354/62

FOREIGN PATENT DOCUMENTS 2741714 3/1978 Fed. Rep. of Germany .
54-98241 8/1979 Japan .

*Primary Examiner*—Russell E. Adams
*Attorney, Agent, or Firm*—Frishauf, Holtz, Goodman and Woodward

[57] ABSTRACT

A light source device for an endoscope comprising a xenon lamp, a lamp drive circuit for supplying current to the xenon lamp for causing the emission of light when a synchronizing signal is supplied from a camera, an integrating circuit for integrating current supplied from the camera and an illumination stop circuit for supplying an illumination stop signal to a lamp drive circuit when the output of said integrating circuit reaches a predetermined value. The device further comprises a first timer circuit for producing a first signal for a first predetermined period of time responsive to the synchronizing signal from the camera, a second timer circuit for producing a second signal for a second predetermined period of time after the time out of the output of the first timer circuit, and a gate circuit for rendering a third timer circuit non-conductive during the presence of the second signal, the synchronizing signal from the camera being supplied through the gate circuit to the lamp drive circuit to cause the xenon lamp to emit light for photographing.

8 Claims, 21 Drawing Figures

LIGHT SOURCE APPARATUS FOR ENDOSCOPE

BACKGROUND OF THE INVENTION

This invention relates to a light source apparatus for an endoscope and, more particularly, to an external light source apparatus used for endoscopic photographing.

Generally, endoscopic photographing is effected concurrently when a body cavity is observed with an endoscope. In endoscopic photographing, the object to be photographed is completely dark so that a shutter need not be provided on the camera, but as a shutter release operation it is only necessary to block light from a light source. For this reason, in the light source apparatus for an endoscope a shutter plate is provided between the light source and a light transmitting means for transmitting light from the light source to an objective lens section in the endoscope. For taking the endoscopic picture an ordinary still camera may be provided at an eyepiece section of the endoscope. During the photographing, the shutter plate of the light source apparatus is held released by a drive means such as a rotary solenoid. Therefore, if the exposure is made for a long time, the drive means is rendered into an overload state. Generally, in endoscopic photographing the object to be photographed is completely dark, and a considerably long time is required for the exposure, so that the afore-mentioned inconvenience arises. Further, while it is required to take pictures at a short interval for examining changes of the affected part of the body, in this case the light source has to be repeatedly on-off operated. This is undesired from the standpoint of the service life of the light source if a discharge lamp is used as the light source.

An object of the invention is to provide a light source apparatus for an endoscope, in which power supplied is controlled for preventing the overload state of the discharge lamp and shutter plate.

SUMMARY OF THE INVENTION

The above object of the invention is achieved by a light source apparatus for an endoscope, which comprises a discharge lamp, a synchronizing terminal for receiving a synchronizing signal synchronized to a shutter release operation from a camera, a signal generating means connected to the synchronizing terminal and being responsive to the synchronizing signal for producing a first signal for a first predetermined period of time and for subsequently producing a second signal for a second predetermined period of time, a gate means connected to the synchronizing terminal and to said signal generating means and being rendered conductive to pass the synchronizing signal according to the first signal in the absence of the second signal and being rendered non-conductive during the presence of the second signal, means connected to the gate means and to said discharge lamp for supplying current for a given period of time which is sufficient to cause the discharge lamp to produce a light does required for endoscopic photographing to the discharge lamp responsive to the output of the gate means.

DETAILED DESCRIPTION

Figure 1:
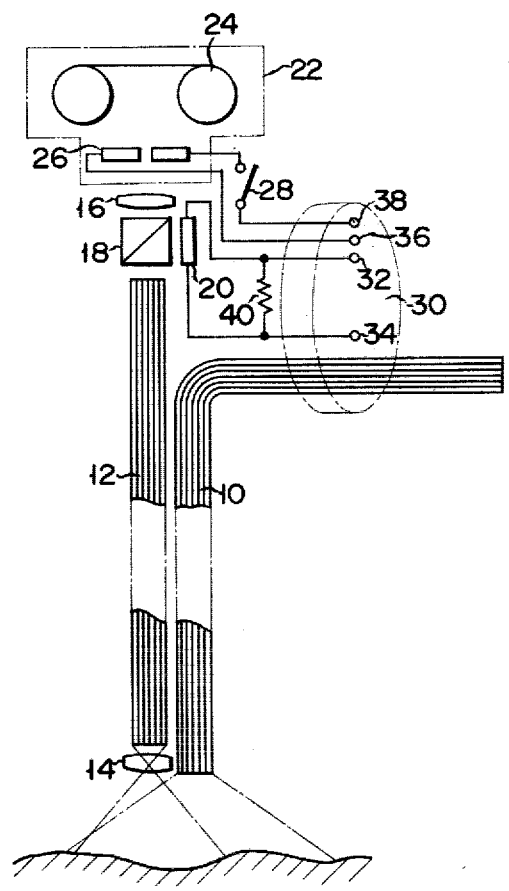
FIG. 1 is a schematic repesentation of an endoscope.

The invention will now be described in conjunction with some preferred embodiments thereof with reference to the accompanying drawings. The general endoscope construction will now be described. FIG. 1 shows a so-called fiberscope with a still camera provided at an eyepiece section for photographing the image obtained thereat. The fiberscope mainly comprises a light guide 10 including an optical-fiber cable for transmitting illumination light and an image guide 12 also including an optical-fiber cable for transmitting the optical image of the visualized scene. An objective lens 14 is provided in an objective section at one end of the image guide 12, and an eyepiece 16 is provided in an eyepiece section at the other end. A half mirror 18 is provided between the eyepiece 16 and image guide 12, and it reflects part of the incident light from the image guide 12 in a direction at right angles to the direction of incidence. On one side of the half mirror 18 is provided a light-receiving element 20 for receiving the reflected light from the half mirror 18. An ordinary single-lens reflex camera 22 is mounted in front of the eyepiece 16. It has film 24, a shutter 26 and a synchronizng switch 28. The light guide 10 includes a portion which is arranged integral with and extended along the image guide 12, with the end of this portion found adjacent to the objective lens 14, and a portion led through a connector 30 to a light source device which will be described later. The connector 30 is provided with light-receiving terminals 32 and 34 to which a signal from the light-receiving element 20 is supplied and also synchronizing terminals 36 and 38 to which a signal from the synchronizing switch 28 is supplied. The signal from the light-receiving element 20 is supplied through a sensitivity adjustment resistor 40 to the terminals 32 and 34.

Figure 2:
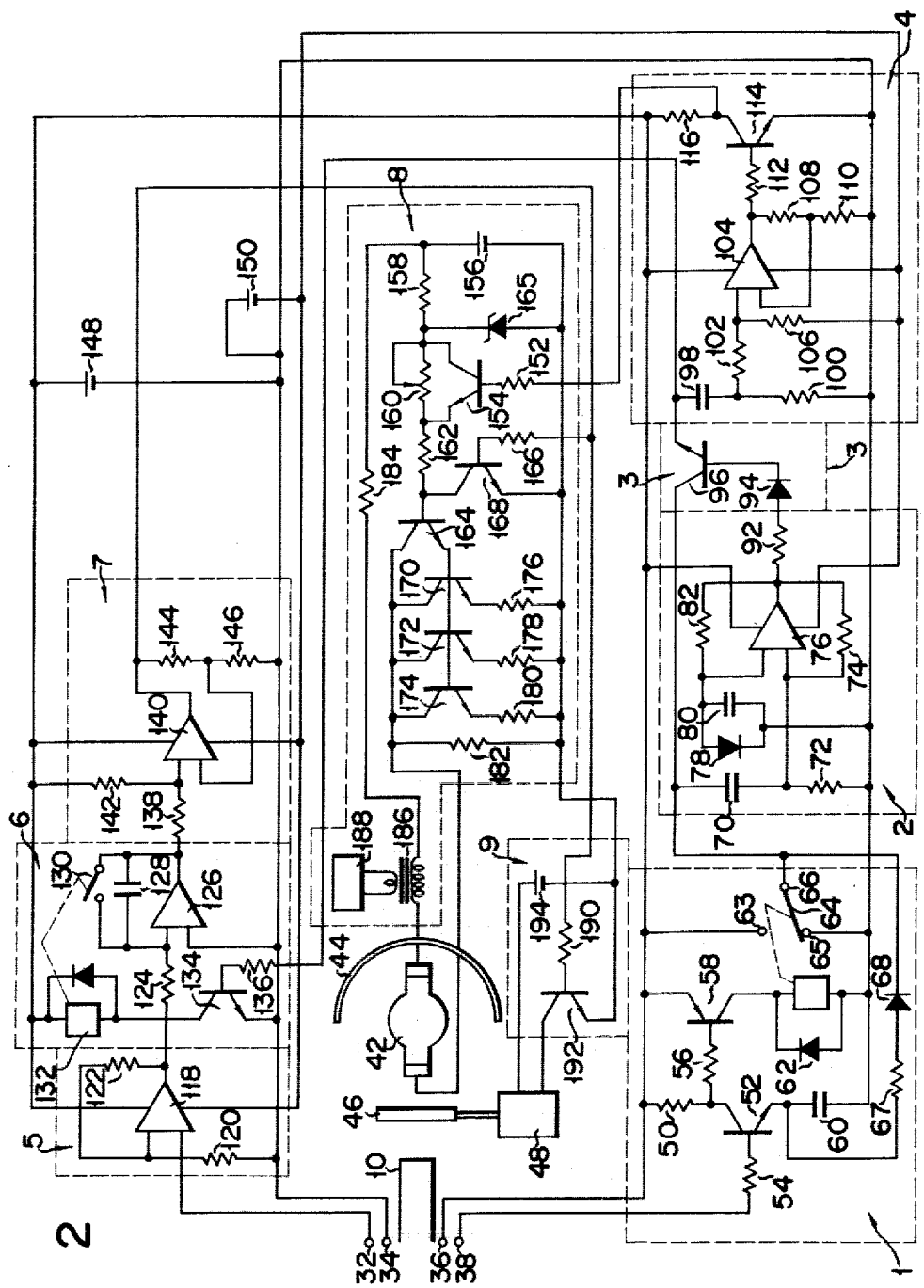
FIG. 2 is a circuit diagram showing an embodiment of the light source apparatus for an endoscope according to the invention.

FIG. 2 shows a circuit diagram of an embodiment of the light source apparatus according to the invention applied to such an endoscope. A xenon lamp 42 is provided as a light source and is disposed such that light from it is incident on the corresponding end of the light guide 10. A reflector 44 is provided on the side of the xenon lamp 42 opposite the light guide 10, and a shutter plate 46 is provided between the xenon lamp 42 and light guide 10. The shutter plate 46 is controlled by a rotary solenoid 48 for blocking the light path between the light guide 10 and xenon lamp 42 or leaving it not blocked. The synchronizing terminal 36 is connected through a resistor 50 to the collector of an NPN transistor 52. The synchronizing terminal 38 is connected through a resistor 54 to the base of the transistor 52. The transistor 52 has its collector connected through a resistor 56 to the base of a PNP transistor 58 and its emitter connected through a capacitor 60 to one terminal of a relay 62. The collector of the transistor 58 is connected to the other terminal of the relay 62. The relay 62 functions to switch the connection state of a relay switch 64, which has its first and second fixed contacts 63 and 65 connected respectively to the synchronizing terminal 36 and the junction between the relay 62 and capacitor 60. The emitter of the transistor 52 is connected through a resistor 67 and diode 68 to a movable contact terminal 66 of the relay switch 64. The above component parts constitute a first timer circuit 1.

The movable contact terminal 66 of the relay switch 64 is connected through a capacitor 70 and resistor 72 to the second fixed contact 65 of the relay switch 64. The junction between the capacitor 70 and resistor 72 is connected to one of input terminals of an operational amplifier 76 and is also connected through a resistor 74 to an output terminal of the operational amplifier 76. A circuit comprising a diode 78 and capacitor 80 in parallel with each other has its one terminal connected to the second fixed contact 65 of the relay switch 64 and its other terminal connected to the other input terminal of the operational amplifier 76. A resistor 82 is connected between this other input terminal and output terminal of the operational amplifier 76. The output terminal of the operational amplifier 76 is connected to one terminal of a resistor 92. The above component parts constitute a second timer circuit 2.

The other terminal of the resistor 92 is connected through a diode 94 to the base of an NPN transistor 96. The diode 94 and transistor 96 constitute a gate circuit 3.

The transistor 96 has its collector connected to the terminal 66 of the movable contact of the relay switch 64 and its emitter connected through a capacitor 98 and resistor 100 to the second fixed contact 65 of the relay switch 64. The junction between the capacitor 98 and resistor 100 is connected through a resistor 102 to one of input terminals of an operational amplifier 104. To this input terminal of the operational amplifier 104 is connected one terminal of resistor 106. The operational amplifier 104 has its output terminal connected through reistors 108 and 110 to the second fixed contact 65 of the relay switch 64 and also connected through a resistor 112 to the base of an NPN transistor 114. The junction between the resistors 108 and 110 is connected to the other input terminal of the operational amplifier 104. The transistor 114 has its emitter connected to the second fixed contact 65 of the relay switch 64 and its collector connected through a resistor 116 to the synchronizing terminal 36. The above component parts constitute a third timer circuit 4.

The light-receiving terminal 32 is connected to one of input terminals of an operational amplifier 118. The light-receiving terminal 34 is connected through a resistor 120 to the other input terminal of the operational amplifier 118. The operational amplifier 118 has its output terminal connected through a resistor 122 to the other input terminal of the operational amplifier 118. The above component parts constitute a DC amplifier circuit 5.

The operational amplifier 118 has its output terminal connected through a resistor 124 to one of input terminals of an operational amplifier 126. The other input terminal of the operational amplifier 126 is connected to the light-receiving terminal 34. The operational amplifier 126 has its output terminal connected through a capacitor 128 to one of input terminals of the first input terminal of the operational amplifier 126. A relay switch 130 is connected between the opposite terminals of the capacitor 128. It is on-off controlled by a relay 132. The relay 132 has one terminal connected to the collector of an NPN transistor 134 and the other terminal connected to the synchronizing terminal 36. The transistor 134 has its emitter connected to the light-receiving terminal 34 and its base connected through a resistor 136 to the emitter of the transistor 96 in the gate circuit 3. The above component parts constitute an integrating circuit 6.

The operational amplifier 126 has its output terminal connected through a resistor 138 to one of input terminals of an operational amplifier 140. The synchronizing terminal 36 is also connected through a resistor 142 the aforesaid input terminal of the operational amplifier 140. The operational amplifier 140 has its output terminal connected through resistors 144 and 146 to the light-receiving terminal 34. The junction between the resistors 144 and 146 is connected to the other input terminal of the operational amplifier 140. The above component parts constitute a level detecting circuit 7.

A power supply 148 has its positive terminal connected to the synchronizing terminal 36 and its negative terminal connected to the second fixed contact 65 of the relay switch 64 in the first timer circuit 1 and also to the light-receiving terminal 34. Another power supply 150 has its positive terminal connected to the negative terminal of the power supply 148 and its negative terminal connected the other terminal of the resistor 106 in the third timer circuit 4. The power supply 148 is a positive voltage source for the operational amplifiers 76, 104, 118, 126 and 140, and the power supply 150 is a negative voltage source for these operational amplifiers.

The transistor 114 in the third timer circuit 4 has its collector connected through a resistor 152 to the base of an NPN transistor 154. A power supply 156 has its positive terminal connected through a series circuit including a resistor 158, variable resistor 160 and resistor 162 to the base of an NPN transistor 164. The transistor 154 has its emitter and collector respectively connected to the opposite terminal of the variable resistor 160. The power supply 156 has its negative terminal connected to the anode of a zener diode 165, which has its cathode connected to the junction between the resistor 158 and variable resistor 160. The operational amplifier 140 in the level detecting circuit 7 has its output terminal connected through a resistor 166 to the base of an NPN transistor 168, which has its collector connected to the base of the transistor 164 and its emitter connected to the negative terminal of the power supply 156. The transistor 164 has its collector connected to the collectors of NPN transistors 170, 172 and 174 and also to one terminal of the xenon lamp 42 and its emitter connected to the bases of the transistors 170, 172 and 174. The transistors 170, 172 and 174 have their emitters connected through respective resistors 176, 178 and 180 to the negative terminal of the power supply 156. A resistor 182 is connected between the collector of the transistor 174 and the negative terminal of the power supply 156. The positive terminal of the power supply 156 is connected through a resistor 184 and a transformer 186 to the other terminal of the xenon lamp 42. The primary winding of the transformer 186 is connected to a high voltage pulse generator 188. The above portions constitute a lamp current control circuit 8.

The output terminal of the level detection circuit 7 is connected through a resistor 190 to the base of an NPN transistor 192. The transistor 192 has its emitter connected to negative terminals of the power supply 156 and a power supply 194 and its collector connected to the negative terminal of the rotary solenoid 48. The positive terminal of the power supply 194 is connected to the positive terminal of the rotary solenoid 48. The above portions constitute a solenoid drive circuit 9.

Figure 3:
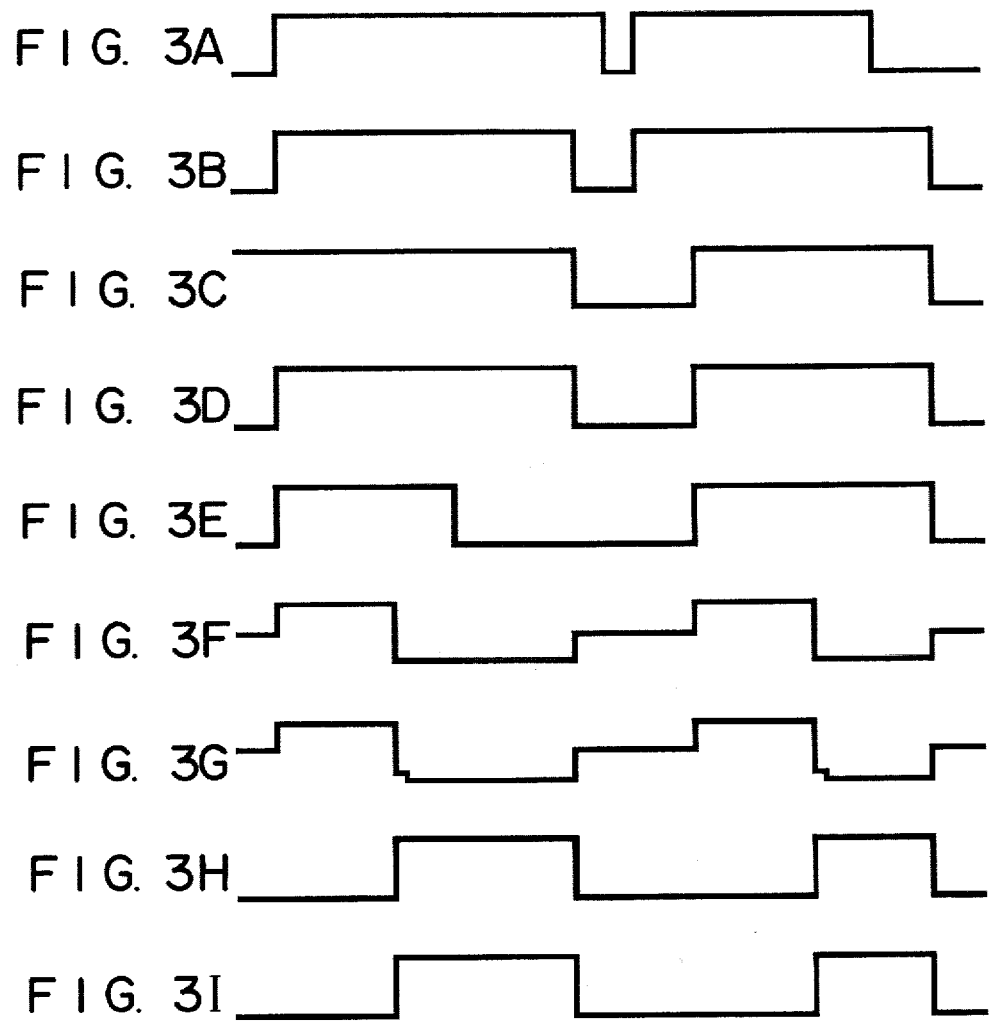
FIGS. 3A to 3I constitute a timing chart for illustrating the operation of the embodiment of FIG. 2.

The operation of the embodiment of the above construction will now be described. The relays 62 and 132 are normally not energized, with the movable contact of relay switch 64 connected to the second fixed contact 65 and relay switch 130 closed. When the shutter 26 of the camera is released for photographing, the synchronizing switch 28 is closed, whereupon the synchronizing terminal 38 is brought to an H (high) level as shown in FIG. 3A. As a result, the transistors 52 and 58 are triggered to energize the relay 62, thus switching the movable contact of relay switch 64 to the side of the first fixed contact 63. Since the first fixed contact 63 of the relay switch 64 is connected to the synchronizing terminal 36, the potential on the movable contact terminal 66, i.e., output terminal of the first timer circuit 1, is inverted to an H level as shown in FIG. 3B. Since the capacitor 60 is charged by the current flowing through the transistor 52, the emitter potential on the transistor 52 is gradually increased. When the terminal voltage across the capacitor 60 exceeds the base voltage on the transistor 52, the transistor 52 is cut off to deenergize the relay 62, thus switching the relay switch 64 again to the side of the second fixed contact 65. The output terminal of the first timer circuit 1 is thus inverted again to an L (low) level after the lapse of a predetermined period of time as shown in FIG. 3B. When the relay switch 64 is switched to the side of the second fixed contact 65, the capacitor 60 is discharged.

When the output signal of the first timer circuit 1 is at the H level, the output signal of the second timer circuit 2 is at an H level. When the output signal of the first timer circuit 1 is inverted to the L level, a negative pulse sufficient to change the output signal of the operational amplifier 76 to an L level appears at the junction between the capacitor 70 and resistor 72, i.e., the aforementioned other input terminal of the operational amplifier 76, because of the presence of the differentiating circuit comprised of the capacitor 70 and resistor 72.

Thus, when the output signal of the first timer circuit 1 is inverted from the H level to the L level, the output of the second timer circuit 2 is also inverted from the H level to the L level as shown in FIG. 3C.

In this state, the capacitor 80 is charged with the time constant of the circuit including the capacitor 80 and resistor 82. When the terminal voltage across the capacitor 80 reaches a predetermined value, the output voltage of the operational amplifier 76 is inverted to an H level. In this way, the output voltage of this operational amplifier 76 is first inverted to the L level and then inverted to the H level again after a predetermined period of time as shown in FIG. 3C. The transistor 96 in the gate circuit 3 is controlled by this output signal. Since the output signal of the first timer circuit 1 is supplied to the collector of the transistor 96, the emitter output of the transistor 96, i.e., the output signal of the gate circuit 3, is inverted to an H level when the output of the first timer circuit 1 is inverted to the H level and is inverted to an L level again when the output signal of the second timer circuit 2 is inverted to the L level even though the output signal of the first timer circuit 1 is at the H level, as shown in FIG. 3D.

When the output signal of the gate circuit 3 is at the H level, the capacitor 98 in the third timer circuit 4 is charged so that the potential on the junction between the capacitor 98 and resistor 100 is gradually increased. When the output signal of the gate circuit 3 is inverted to the H level, the output signal of the operational amplifier 104 is inverted to an L level to cut off the transistor 114. As a result, the collector output of the transistor 114, i.e., the output signal of the third timer circuit 4, is inverted to an H level as shown in FIG. 3E. At an instant during the charging of the capacitor 98, namely at an instant when the quotient of division of the potential of the power supply 150 by the resistance of the resistor 106 becomes less than the quotient of division of the potential at the junction between the capacitor 98 and resistor 100 by the resistance of the resistor 102, the output signal of operational amplifier 104 is inverted to an H level to trigger the transistor 114. Thus, the output signal of the third timer circuit 4 is inverted to the L level after the lapse of a predetermined period of time as shown in FIG. 3E.

Since the output signal of the third timer circuit 4 is supplied to the lamp current control circuit 8, the lamp current control circuit 8 is driven only when the output signal of the third timer circuit 4 is at the H level. While the third timer circuit 4 provides the H level signal for a predetermined period of time from the instant when the output signal of the gate circuit 3 is inverted to the H level, the gate circuit 3 produces no output signal when the output signal of the second timer circuit 2 is at the L level even though the H level output signal is produced from the first timer circuit 1 when the synchronizing terminal 38 is brought to the H level. In other words, the lamp current control circuit 8 is held in an inoperative state at least during the period, during which the output signal of the second timer circuit 2 is at the L level, so that it is possible to prevent the xenon lamp 42 from being energized intermittently at a short interval.

When the output signal of the third timer circuit 4 is at the L level, the transistor 154 in the lamp current control circuit 8 is not in conduction, and the current through the xenon lamp 42 is at a certain value determined by the variable resistor 160 as shown in FIG. 3F. Thus, before the camera shutter is released, the light dose provided by the light guide 10 is set to a suitable brightness for endoscopic observation as shown in FIG. 3G. With the inversion of the output signal of the third timer circuit 4 to the H level, at which time the transistor 154 is triggered, the variable resistor 160 is shunted so that the current through the xenon lamp 42 is increased as shown in FIG. 3F.

Meanwhile, the solenoid drive circuit 9 is normally not driven as shown in FIG. 3H, so that the shutter plate 46 is held at a position not to block light from the xenon lamp 42. Thus, at this time the light dose provided by the light guide 10 is increased corresponding to the dose of light from the xenon lamp 42 as shown in FIG. 3G. Light transmitted through the light guide 10 at this time thus illuminates the scene, which is to be photographed, and the image of the scene is led through the objective lens 14 and image guide 12 to the film 24, whereby the photographing is obtained. The image of the scene is also coupled through the half mirror 18 to the light-receiving element 20. The light-receiving element 20 produces a photo-current corresponding to the received light dose, and this photo-current is converted into a corresponding voltage through the sensitivity adjustment resistor 40. This voltage is amplified through the DC amplifier 5 to $(R_{120}+R_{122})/R_{120}$ times before it is coupled to the integrating circuit 6. Meanwhile, with the inversion of the output signal of the gate circuit 3 to the H level, the relay 132 is energized to open the relay switch 130. When the relay switch 130 is opened, the output signal of the operational amplifier 126 is integrated by the capacitor 128. The output of the integrating circuit 6 is supplied to the level detection circuit 7, and when the quotient of division of the output voltage of the integrating circuit 6 by the resistor 138 reaches the quotient of division of the voltage of the power supply 148 by the resistance of the resistor 142, the output signal of the level detection circuit 7 is inverted to an H level as shown in FIG. 3I. The output signal of the level detection circuit 7 is coupled through the lamp current control circuit 8 and solenoid drive circuit 9. As a result, the transistor 168 in the lamp current control circuit 8 is triggered to cut off all of the transistors 174, 172, 170 and 164, and a current determined by the resistor 182 is thus caused to flow through the xenon lamp 182 as shown in FIG. 3F. The resistance of the resistor 182 is set such that a minimum current which can sustain the discharge in the xenon lamp 42 flows through it. While it is ideal that this current is zero, this is not made so because for resuming the discharge a high voltage is required, which is dangerous to the body. When the solenoid drive circuit 9 is energized by the output of the level detection circuit 7 and produces an H level output signal as shown in FIG. 3H, the solenoid 48 is driven. As a result, the shutter plate 46 is caused to block light from the xenon lamp 42. Since a slight delay time is involved in the response of the solenoid 48, the light dose of the light guide 10 is completely reduced to zero after it is reduced to a level corresponding to the minimum current capable of sustaninng the discharge in the xenon lamp 42 as shown in FIG. 3G. At this instant the camera shutter is still held released as shown in FIG. 3A, but with the reduction of the light dose of the light guide 10 to zero, the end is brought to the photographing of the scene at this time.

The output signal of the first timer circuit 1 is inverted to the L level a predetermined period of time after its inversion to the H level with the releasing of the camera shutter. When the synchronizing terminal is subsequently brought to the H level, no current for causing emission of light by the xenon lamp 42 is caused so long as the output signal of the second timer circuit 2 is at the L level. When the output signal of the second timer circuit 2 is inverted to the H level, the lamp 42 is turned on to effect photographing. Since the interval of absence of the output pulse of the second timer circuit 2 determines the on-off interval of the current supply to the xenon lamp 42, long life of the lamp can be ensured. In addition, since the duration of the output pulse of the first timer circuit 1 determines the longest exposure period, it is possible to take pictures without taking care of the overload of the shutter plate drive solenoid.

Figure 4:
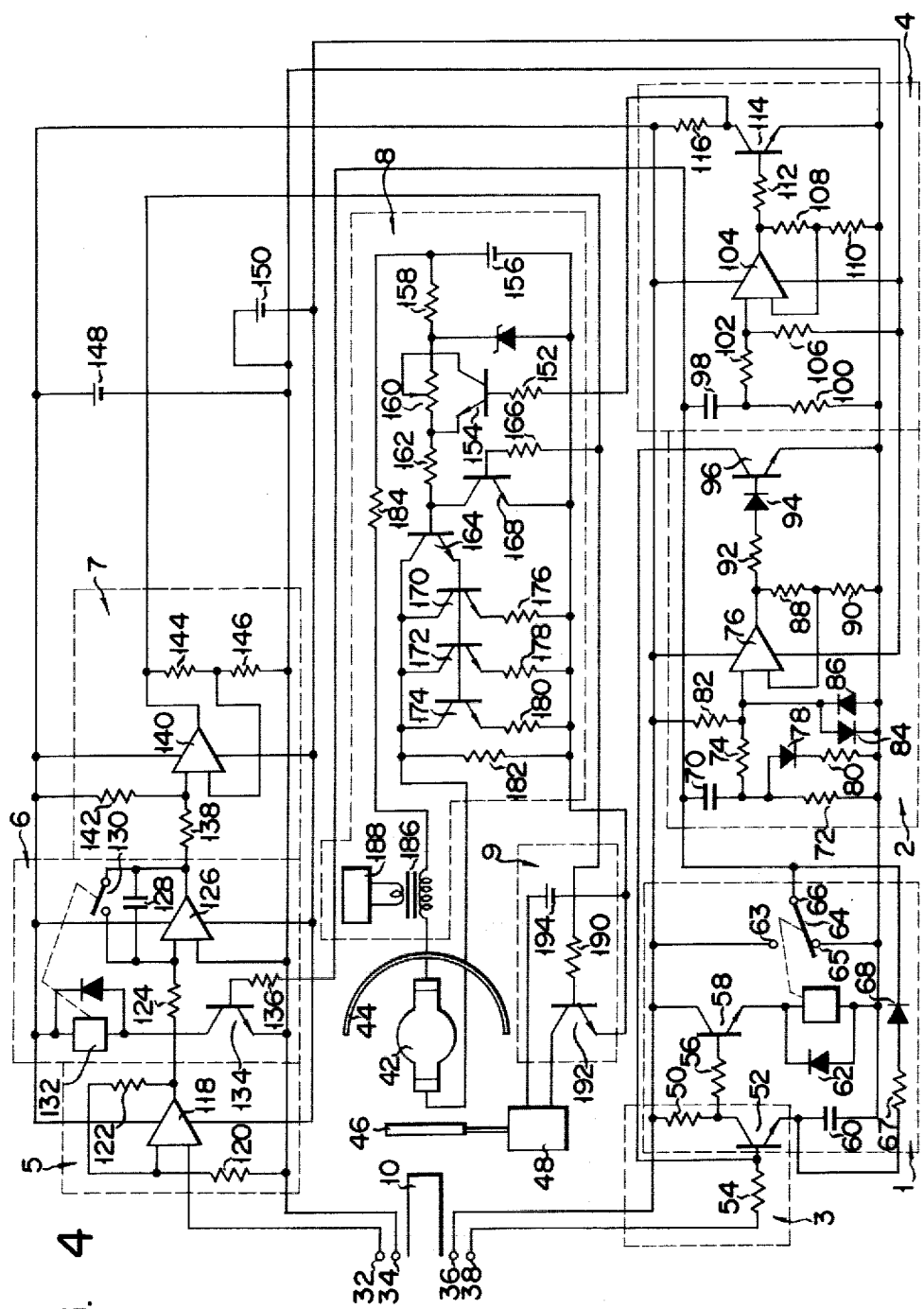
FIG. 4 is a circuit diagram showing another embodiment of the light source apparatus for an endoscope according to the invention.

FIG. 4 shows a circuit diagram of a second embodiment of the invention. In FIG. 4, like parts as those in FIG. 2 are designated by like reference numerals, and they are not described here. In this embodiment, a diode 94 and transistor 96, which have constituted the gate circuit 3 in the preceding embodiment of FIG. 2, belong to a second timer circuit 2, with the collector of the transistor 96 connected to the base of a transistor 52 in a first timer circuit 1.

Figure 5A:
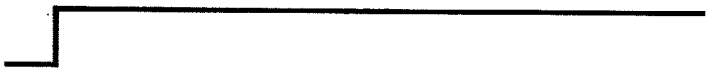
FIGS. 5A to 5I constitute a time chart for illustrating the operation of the embodiment of FIG. 4.
Figure 5B:
Figure 5C:
Figure 5D:
Figure 5E:
Figure 5F:
Figure 5G:
Figure 5H:
Figure 5I:

The transistor 52 in the first timer circuit 1 constitutes a gate circuit 3 together with resistors 50 and 54. FIGS. 5A to 5I constitute a time chart showing the waveforms appearing in various parts in the embodiment of FIG. 4 corresponding to those shown in FIGS. 3A to 3I. The operation of the embodiment of FIG. 4 will now be described. It is assumed that the camera shutter remains released so that the synchronizing terminal 38 is held at the H level as shown in FIG. 5A due to a malfunction of the camera. When the synchronizing terminal 38 is brought to the H level, the output signal of the gate circuit 3 is inverted to an H level as shown in FIG. 5D. As a result, an H level signal is produced from the first timer circuit 1 as shown in FIG. 5B, causing the third timer circuit 4 to produce an H level signal as shown in FIG. 5E. The aforementioned photographing operation is effected when the output signal of the third timer circuit 4 is at the H level. When the output signal of the first timer circuit 1 is inverted to an L level after the lapse of a predetermined period of time as shown in FIG. 5B, the output signal of the second timer circuit 2 is inverted to the H level as shown in FIG. 5C. The gate circuit 3 is rendered non-conductive by the H level output signal of the second timer circuit 2. Thus, even though the synchronizing terminal 38 is at the H level, the output signal of the first timer circuit 1 is not inverted to the H level so that the output signal of the third timer circuit 4 is not inverted to the H level. In this way, the photographing operation is inhibited. The photographing operation is effected again when the output signal of the second timer circuit 2 is subsequently inverted to the L level again.

In the above way, in the second embodiment even with the shutter held continuously released, the photographing operation can be effected at a predetermined interval, and the light source is turned on for every photographing operation to let the observer know a faulty state and take a proper countermeasure.

What is claimed is:

1. A light source apparatus for a photographing endoscope arrangement for use with a camera, comprising:
   light-emitting means;
   a synchronizing terminal for receiving a synchronizing signal synchronized to a shutter release operation from a camera;
   signal generating means coupled to said synchronizing terminal and being responsive to said synchronizing signal for producing a first signal for a first predetermined period of time and for subsequently producing a second signal for a second predetermined period of time;
   gate means coupled to said synchronizing terminal and to said signal generating means and rendered conductive to pass said synchronizing signal to an output of the gate means responsive to said first signal and in the absence of said second signal, said gate means being rendered non-conductive so as not to pass said synchronizing signal during the presence of said second signal; and
   energizing means coupled to the output of said gate means and to said light-emitting means for causing said light-emitting means to produce a light dose required for photographing by enabling said light-emitting means for a third predetermined period of time responsive to the output of said gate means.

2. A light source apparatus for an endoscope according to claim 1, further comprising:
   a light-receiving terminal for receiving photo-current information corresponding to the light dose received at the camera;
   arithmetic means connected to said light-receiving terminal for integrating said photo-current information and producing an illumination stop signal when the integration value reaches a predetermined value; and a shutter member for blocking light transmitted from said light-emitting means to the camera responsive to said illumination stop signal produced from said arithmetic means.

3. A light source apparatus for an endoscope according to claim 2, wherein said energizing means normally causes said light-emitting means to produce a light dose required for endoscopic observation and causes said light-emitting means to produce a minimum light dose required for endoscopic observation responsive to said illumination stop signal produced from said arithmetic means.

4. A light source apparatus for an endoscope according to claim 1, wherein said light-emitting means comprises a discharge lamp; and said energizing means includes a current controlling variable resistor; current controlled by said variable resistor being supplied to said light-emitting means.

5. A light source apparatus for an endoscope according to claim 1, wherein said signal generating means comprises a first timer circuit coupled to said synchronizing terminal for producing said first signal for said first predetermined period of time; and a second timer circuit coupled to the output of said first timer circuit for producing said second signal for said second predetermined period of time after termination of said first signal.

6. A light source apparatus for an endoscope according to claim 1 or claim 5, wherein said energizing means comprises a third timer circuit coupled to said output of said gate means for producing a third signal for a third predetermined period of time for enabling said light emitting means for said third predetermined period of time for producing said light dose required for photographing.

7. A light source apparatus for an endoscope according to claim 6, wherein said third predetermined period of time is less than said first predetermined period of time.

8. A light source apparatus for an endoscope according to claim 1, wherein said third predetermined period of time is less than said first predetermined period of time.

* * * * *